US012396840B2

(12) United States Patent
Mejia et al.

(10) Patent No.: US 12,396,840 B2
(45) Date of Patent: Aug. 26, 2025

(54) BREAST IMPLANTS WITH INTEGRATED TRANSPONDERS

(71) Applicant: ESTABLISHMENT LABS S.A., Alajuela (CR)

(72) Inventors: Ezequiel Mejia, Woodbury, MN (US); Randolph Keith Geissler, Minneapolis, MN (US); Juan José Chacón Quirós, Alajuela (CR)

(73) Assignee: Establishment Labs S.A., Alajuela (CR)

( * ) Notice: Subject to any disclaimer, the term of this patent is extended or adjusted under 35 U.S.C. 154(b) by 0 days.

(21) Appl. No.: 18/204,087

(22) Filed: May 31, 2023

(65) Prior Publication Data
US 2023/0301772 A1    Sep. 28, 2023

Related U.S. Application Data

(63) Continuation of application No. 16/832,149, filed on Mar. 27, 2020, now Pat. No. 11,701,219, which is a
(Continued)

(51) Int. Cl.
*A61F 2/12* (2006.01)
*B29C 41/02* (2006.01)
(Continued)

(52) U.S. Cl.
CPC .............. *A61F 2/12* (2013.01); *B29C 41/02* (2013.01); *B29C 41/14* (2013.01);
(Continued)

(58) Field of Classification Search
CPC ...... A61F 2/12; A61F 2/02; A61F 2250/0002; A61F 2250/0096; A61F 2250/0085;
(Continued)

(56) References Cited

U.S. PATENT DOCUMENTS 4,863,470 A * 9/1989 Carter ..................... A61F 2/12
                                                        623/8
5,300,120 A   4/1994 Knapp et al.
(Continued)

FOREIGN PATENT DOCUMENTS

BR    112015005695 A2    7/2017
BR    112015005695 B1    11/2021
(Continued)

OTHER PUBLICATIONS

U.S. Appl. No. 15/868,414 U.S. Pat. No. 10,631,976, filed Jan. 11, 2018, Method of Manufacturing Breast Implants With Integrated Transponders.
(Continued)

*Primary Examiner* — Seema Mathew
(74) *Attorney, Agent, or Firm* — SCHWEGMAN LUNDBERG & WOESSNER, P.A.

(57) ABSTRACT

The present disclosure provides, in various examples, an implant with a transponder embedded therein, and a method of identifying the implant while inside the human body. In certain examples, the method includes, for example, identifying an implant with an external reader and establishing a wireless communication between the external reader and the transponder. In an example, the implant is identified using information obtained during the wireless communication.

20 Claims, 2 Drawing Sheets

Related U.S. Application Data continuation of application No. 15/868,414, filed on Jan. 11, 2018, now Pat. No. 10,631,976, which is a continuation of application No. 14/028,193, filed on Sep. 16, 2013, now Pat. No. 9,901,438.

(60) Provisional application No. 61/701,910, filed on Sep. 17, 2012.

(51) Int. Cl.
  *B29C 41/14* (2006.01)
  *B29L 31/00* (2006.01)

(52) U.S. Cl.
  CPC . *A61F 2240/001* (2013.01); *A61F 2250/0096* (2013.01); *B29L 2031/7532* (2013.01)

(58) Field of Classification Search
  CPC ........ A61F 2210/0076; A61F 2240/001; A61F 2250/0003; A61F 5/003; A61F 2/0059; A61F 2/52; A61F 5/0033; A61F 2/26; A61F 2002/3071; A61B 90/02; A61B 90/39; A61B 90/98; A61B 2562/08
  See application file for complete search history.

(56) References Cited

U.S. PATENT DOCUMENTS

| | | | |
|---|---|---|---|
| 5,545,220 A | 8/1996 | Andrews et al. | |
| 5,653,758 A | 8/1997 | Daniels et al. | |
| 5,674,288 A | 10/1997 | Knapp et al. | |
| 5,716,407 A | 2/1998 | Knapp et al. | |
| 5,725,578 A | 3/1998 | Knapp et al. | |
| 5,824,081 A | 10/1998 | Knapp et al. | |
| 5,833,603 A | 11/1998 | Kovacs et al. | |
| 5,855,609 A | 1/1999 | Knapp | |
| 5,977,431 A | 11/1999 | Knapp et al. | |
| 8,042,738 B2 | 10/2011 | Cloix | |
| 8,764,825 B2 | 7/2014 | Ledergerber | |
| 9,132,004 B2* | 9/2015 | Yu | B29C 66/12822 |
| 9,901,438 B2 | 2/2018 | Mejia et al. | |
| 10,052,190 B2* | 8/2018 | Chitre | A61B 90/02 |
| 10,588,737 B2* | 3/2020 | Mcclellan | A61F 2/12 |
| 10,631,976 B2 | 4/2020 | Mejia et al. | |
| 11,160,630 B2* | 11/2021 | Schuessler | A61F 2/12 |
| 11,701,219 B2 | 7/2023 | Mejia et al. | |
| 2006/0069403 A1* | 3/2006 | Shalon | A61F 2/12 |
| | | | 606/192 |
| 2006/0111777 A1* | 5/2006 | Chen | G08B 21/18 |
| | | | 128/903 |
| 2007/0239016 A1* | 10/2007 | Fisher | A61F 2/02 |
| | | | 600/458 |
| 2008/0048855 A1* | 2/2008 | Berger | A61B 90/98 |
| | | | 340/539.12 |
| 2008/0270985 A1 | 10/2008 | Mccormack et al. | |
| 2008/0275327 A1* | 11/2008 | Faarbaek | A61B 5/6833 |
| | | | 600/382 |
| 2009/0012372 A1 | 1/2009 | Burnett et al. | |
| 2009/0043177 A1* | 2/2009 | Milledge | A61B 5/0031 |
| | | | 600/309 |
| 2009/0149953 A1* | 6/2009 | Schuessler | A61F 2/12 |
| | | | 623/8 |
| 2009/0270985 A1* | 10/2009 | Schuessler | A61F 5/0036 |
| | | | 623/8 |
| 2010/0049316 A1 | 2/2010 | Schuessler | |
| 2010/0094416 A1* | 4/2010 | Maguire | A61L 27/52 |
| | | | 623/8 |
| 2010/0194541 A1* | 8/2010 | Stevenson | A61B 90/98 |
| | | | 340/10.1 |
| 2010/0228347 A1 | 9/2010 | Schuessler | |
| 2011/0029076 A1 | 2/2011 | Paletta et al. | |
| 2011/0046729 A1* | 2/2011 | Schuessler | A61L 27/26 |
| | | | 264/270 |
| 2011/0098576 A1* | 4/2011 | Hollstien | A61B 5/4851 |
| | | | 600/476 |
| 2011/0137413 A1 | 6/2011 | Osypka | |
| 2011/0257743 A1 | 10/2011 | Schuessler | |
| 2012/0165934 A1 | 6/2012 | Schuessler | |
| 2012/0302874 A1* | 11/2012 | Hollstien | A61B 5/0084 |
| | | | 600/476 |
| 2013/0013063 A1 | 1/2013 | Del Vecchio | |
| 2013/0131800 A1 | 5/2013 | Schuessler | |
| 2013/0338769 A1 | 12/2013 | Boyden et al. | |
| 2013/0338772 A1* | 12/2013 | Boyden | A61B 5/6867 |
| | | | 623/8 |
| 2014/0081398 A1 | 3/2014 | Mejia et al. | |
| 2016/0101281 A1* | 4/2016 | Chen | A61F 5/0033 |
| | | | 623/8 |
| 2018/0036115 A1* | 2/2018 | Smirnov | A61F 2/12 |
| 2018/0200043 A1 | 7/2018 | Mejia et al. | |
| 2019/0038496 A1* | 2/2019 | Levesque | A61H 23/0245 |
| 2019/0142574 A1* | 5/2019 | Quirós | A61F 2/12 |
| | | | 623/8 |
| 2019/0192280 A1* | 6/2019 | Govari | A61B 5/742 |
| 2020/0323624 A1 | 10/2020 | Mejia et al. | |
| 2020/0352704 A1* | 11/2020 | Schuessler | A61F 2/12 |
| 2024/0122480 A1* | 4/2024 | Kim | A61B 5/686 |

FOREIGN PATENT DOCUMENTS

| | | | | |
|---|---|---|---|---|
| EP | 2895109 A1 | 7/2015 | | |
| EP | 2895109 B1 | 1/2019 | | |
| EP | 3479796 A1 | 5/2019 | | |
| EP | 3479796 B1 | 12/2020 | | |
| EP | 3831341 A1 | 6/2021 | | |
| ES | 2721007 T3 | 7/2019 | | |
| HK | 40044710 | 10/2021 | | |
| WO | WO-9404094 A1 * | 3/1994 | ........... A01K 11/006 |
| WO | WO-9622058 A1 | 7/1996 | | |
| WO | WO-2008014283 A2 | 1/2008 | | |
| WO | WO-2008043921 A2 | 4/2008 | | |
| WO | WO-2008055229 A2 | 5/2008 | | |
| WO | WO-2010056610 A2 | 5/2010 | | |
| WO | WO-2014047013 A1 | 3/2014 | | |
| WO | WO-2017137853 A2 | 8/2017 | | |
| WO | WO-2021101232 A1 * | 5/2021 | ........... A61B 5/0002 |

OTHER PUBLICATIONS

U.S. Appl. No. 14/028,193 U.S. Pat. No. 9,901,438, filed Sep. 16, 2013, Method of Manufacturing Breast Implants With Integrated Transponders.

U.S. Appl. No. 16/832,149, filed Mar. 27, 2020, Breast Implants With Integrated Transponders.

"U.S. Appl. No. 14/028,193, Examiner Interview Summary mailed Jul. 6, 2017", 3 pgs.

"U.S. Appl. No. 14/028,193, Final Office Action mailed Apr. 10, 2017", 11 pgs.

"U.S. Appl. No. 14/028,193, Non Final Office Action mailed Oct. 8, 2015", 7 pgs.

"U.S. Appl. No. 14/028,193, Notice of Allowance mailed Oct. 12, 2017", 8 pgs.

"U.S. Appl. No. 14/028,193, Response filed Apr. 8, 2016 to Non Final Office Action mailed Oct. 8, 2015", 10 pgs.

"U.S. Appl. No. 14/028,193, Response filed Jul. 28, 2015 to Restriction Requirement mailed May 5, 2015", 7 pgs.

"U.S. Appl. No. 14/028,193, Response filed Sep. 12, 2016 to Non Final Office Action mailed Oct. 8, 2015", 12 pgs.

"U.S. Appl. No. 14/028,193, Response filed Sep. 25, 2017 to Final Office Action mailed Apr. 10, 2017", 10 pgs.

"U.S. Appl. No. 14/028,193, Restriction Requirement mailed May 5, 2015", 8 pgs.

"U.S. Appl. No. 15/868,414, Non Final Office Action mailed Jul. 29, 2019", 5 pgs.

"U.S. Appl. No. 15/868,414, Notice of Allowance mailed Dec. 27, 2019", 8pgs.

"U.S. Appl. No. 15/868,414, Preliminary Amendment filed Jan. 11, 2018", 3 pgs.

(56) References Cited

OTHER PUBLICATIONS

"U.S. Appl. No. 15/868,414, Response filed Nov. 27, 2019 to Non Final Office Action mailed Jul. 29, 2019", 8 pgs.
"U.S. Appl. No. 15/868,414, Supplemental Preliminary Amendment filed Apr. 5, 2018", 6 pgs.
"U.S. Appl. No. 16/832,149, Non Final Office Action mailed Jun. 20, 2022", 11 pgs.
"U.S. Appl. No. 16/832,149, Notice of Allowance mailed Mar. 1, 2023", 9 pgs.
"U.S. Appl. No. 16/832,149, Preliminary Amendment filed Mar. 27, 2020", 3 pgs.
"U.S. Appl. No. 16/832,149, Response filed Sep. 20, 2022 to Non Final Office Action malled Jun. 20, 2022", 11 pgs.
"U.S. Appl. No. 16/832,149, Supplemental Notice of Allowability mailed May 17, 2023", 2 pgs.
"U.S. Appl. No. 16/832,149, Supplemental Preliminary Amendment filed Jul. 8, 2020", 6 pgs.
"Brazilian Application Serial No. BR112015005695-4, Office Action mailed Mar. 3, 2021", w/ English Machine Translation, 8 pgs.
"Brazilian Application Serial No. BR112015005695-4, Office Action mailed Aug. 20, 2021", w/ English Machine Translation, 6 pgs.
"Brazilian Application Serial No. BR112015005695-4, Office Action mailed Nov. 4, 2019", w/ English Machine Translation, 8 pgs.
"European Application Serial No. 13839796.3, Communication Pursuant to Article 94(3) EPC mailed Apr. 19, 2018", 4 pgs.
"European Application Serial No. 13839796.3, Communication Pursuant to Article 94(3) EPC mailed Aug. 16, 2017", 4 pgs.
"European Application Serial No. 13839796.3, Decision to Grant mailed Dec. 20, 2018", 2 pgs.
"European Application Serial No. 13839796.3, Extended European Search Report mailed Apr. 8, 2016", 9 pgs.
"European Application Serial No. 13839796.3, Intention to Grant mailed Jul. 23, 2018", 30 pgs.
"European Application Serial No. 13839796.3, Response filed Feb. 23, 2018 to Communication Pursuant to Article 94(3) EPC mailed Aug. 16, 2017", 12 pgs.
"European Application Serial No. 13839796.3, Response filed Jun. 26, 2018 to Communication Pursuant to Article 94(3) EPC mailed Apr. 19, 2018", 8 pgs.
"European Application Serial No. 13839796.3, Response filed Nov. 4, 2016 to Extended European Search Report mailed Apr. 8, 2016", 16 pgs.
"European Application Serial No. 18210589.0, Communication Pursuant to Article 94(3) EPC mailed Aug. 30, 2019", 3 pgs.
"European Application Serial No. 18210589.0, Decision to Grant mailed Nov. 26, 2020", 2 pgs.
"European Application Serial No. 18210589.0, Extended European Search Report mailed Apr. 4, 2019", 5 pgs.
"European Application Serial No. 18210589.0, Intention to Grant mailed Feb. 26, 2020", 18 pgs.
"European Application Serial No. 18210589.0, Intention to Grant mailed Jul. 6, 2020", 18 pgs.
"European Application Serial No. 18210589.0, Response filed Jan. 9, 2020 to Communication Pursuant to Article 94(3) EPC mailed Aug. 30, 2019", 16 pgs.
"European Application Serial No. 18210589.0, Response filed May 19, 2020 to Intention to Grant mailed Feb. 26, 2020", 3 pgs.
"European Application Serial No. 20216184.0, Extended European Search Report mailed May 3, 2021", 8 pgs.
"European Application Serial No. 20216184.0, Response filed Dec. 8, 2021 to Extended European Search Report mailed May 3, 2021", 7 pgs.
"International Application Serial No. PCT/US2013/059988, International Preliminary Report on Patentability malled Mar. 26, 2015", 7 pgs.
"International Application Serial No. PCT/US2013/059988, International Search Report mailed Dec. 5, 2013", 3 pgs.
"International Application Serial No. PCT/US2013/059988, Written Opinion mailed Dec. 5, 2013", 5 pgs.

* cited by examiner

BREAST IMPLANTS WITH INTEGRATED TRANSPONDERS

RELATED APPLICATIONS

This application claims the benefit of, and priority to, U.S. Provisional Application No. 61/701,910, filed Sep. 17, 2012, entitled "Breast Implants With Integrated Transponders," which is incorporated herein by reference in its entirety.

BACKGROUND

Currently there is no accurate, adequate, practical or economical way to identify a breast implant that is already inside the body of a patient. This void has developed into a serious complication for the fulfillment of recalls and controls, when the patients do not have the identification information for their implants, or when medical records are not available. More specifically, and relating to defective breast implants which have been already found in the market, many women around the world face the problem of having no information regarding the breast implants inside them, and no way of finding out if they need to be explanted or not, without undergoing an actual explantation procedure. Thus, there is a need in the art for breast implants that, when implanted, can be easily and accurately identified from outside the body.

SUMMARY

The present invention relates to a breast implant designed to add to or replace volume of the breast, which includes a unique device identifier (UDI) therein, providing post-implantation device recognition and traceability. In preferred embodiments, the UDI is a passive RFID (radio frequency identification) transponder, which is embedded within the implant filling at the time of manufacture.

In various embodiments, the present invention provides breast implant comprising a silicone elastomer shell with an opening covered by a patch, a silicone gel filling said shell, and a transponder disposed within said filling and positioned proximal to said patch.

The silicone elastomer shell is formed by preparing a silicone elastomer dispersion; dipping a mold into said dispersion one or more times, forming one or more silicone elastomer layers; and removing the one or more layers from the mold, forming a silicone elastomer shell having an opening where the mold was removed.

In some embodiments, the transponder is placed within the shell through said opening. Said opening is then covered with a patch and the patched shell is filled with a silicone gel through a filling hole in the patch.

In other embodiments, said opening is covered with a patch, the patched shell is filled with a silicone gel through a filling hole in the patch, and the transponder is placed within the patched shell through said filling hole.

In still further embodiments, said opening is covered with a patch, the transponder is placed within the patched shell through a filling hole in the patch, and the patched shell is filled with a silicone gel through said filling hole.

The manufacturing process further includes applying a vacuum to the silicone gel-filled shell, removing air bubbles and positioning the transponder proximal to said patch; sealing the filling hole; and curing the silicone gel, wherein said gel curing further positions the transponder proximal to said patch and comprises heating the silicone-gel filled shell with transponder therein to a temperature of about 140° C. to 200° C. for up to about 8 hours.

In some embodiments, the breast implant with integrated transponder is further sterilized at a temperature of about 120° C. to 150° C. for up to about 36 hours.

Additional features and advantages of the present invention are described further below. This summary section is meant merely to illustrate certain features of the invention, and is not meant to limit the scope of the invention in any way. The failure to discuss a specific feature or embodiment of the invention, or the inclusion of one or more features in this summary section, should not be construed to limit the invention as claimed.

BRIEF DESCRIPTION OF THE DRAWINGS

The foregoing summary, as well as the following detailed description of the preferred embodiments of the application, will be better understood when read in conjunction with the appended drawings. For the purposes of illustrating the device of the present application, there are shown in the drawings preferred embodiments. It should be understood, however, that the application is not limited to the precise arrangements and instrumentalities shown. In the drawings.

DETAILED DESCRIPTION

The present invention provides, in various embodiments, a breast implant with an RFID transponder embedded therein, so that the implant can be conveniently identified while inside the human body, and methods of making the same. The transponder contains a unique identification code and/or implant-specific information that is readily accessible, for example, by an external handheld scanner. In some embodiments, identification information from the transponder can be used to access one or more databases containing further information (regarding the specific breast implant, the specific patient, etc.).

Figure 1:
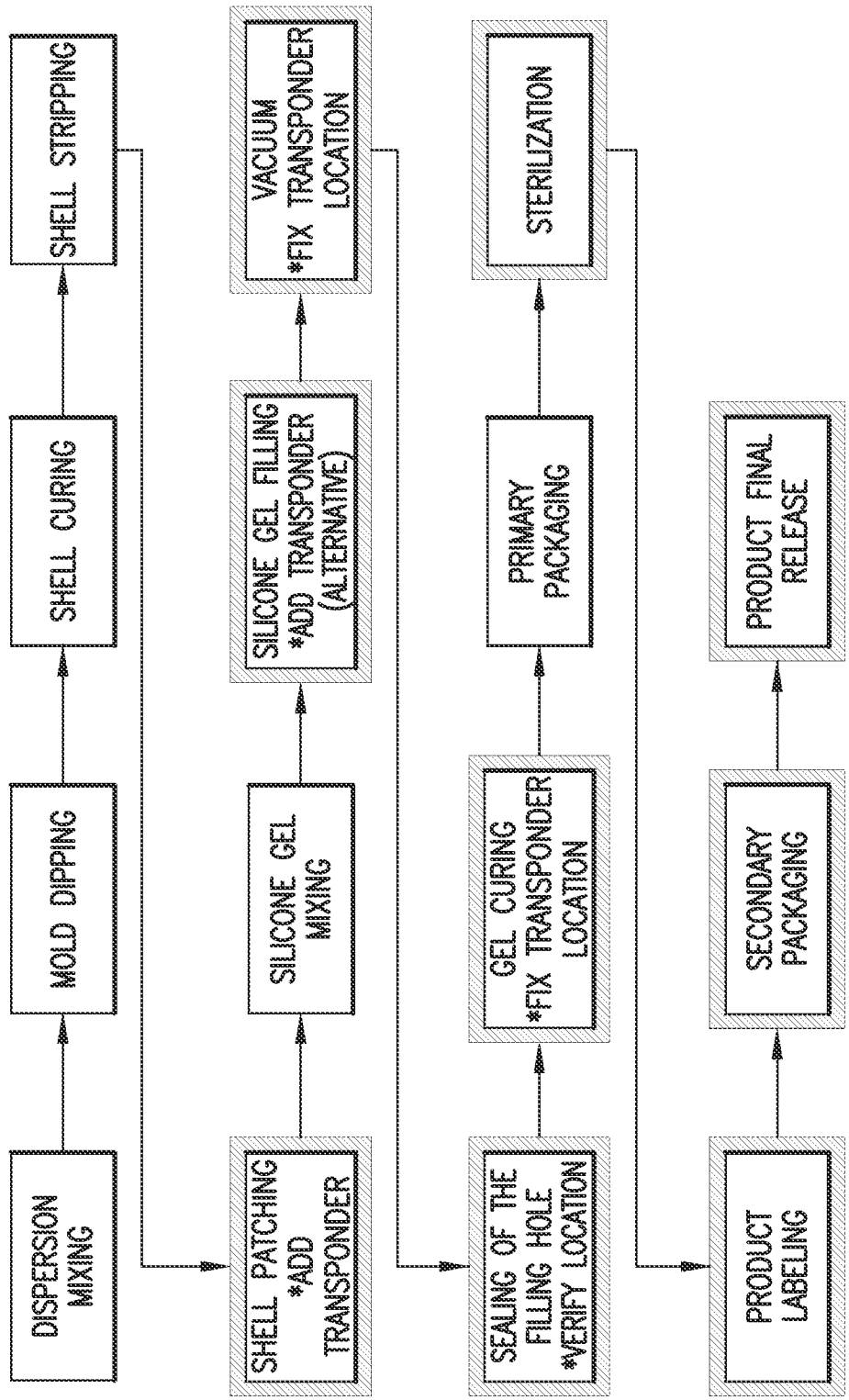
FIG. 1 shows a flowchart of exemplary processes involved in manufacturing the breast implants of the present invention, according to some embodiments.

FIG. 1 shows an exemplary flowchart of the different processes involved in the manufacturing of a breast implant of the present invention, according to some embodiments. The processes affected by inclusion of a transponder are highlighted, and points where the transponder is added/fixed/verified are marked with an asterisk.

In some embodiments, the breast implant comprises a silicone elastomer shell. As shown in FIG. 1, this shell may be formed by preparing/mixing a silicone elastomer dispersion, and dipping a mold or mandrel into the dispersion. Multiple dip coats may be used to obtain a multilayered shell, and different dispersions may be used for different dip coats. For example, a colored barrier layer may be added to the shell, as described in U.S. application Ser. No. 13/412,221. The shell is then cured and removed/stripped from the mold.

The aperture (open part of the shell where the mold was removed) is then patched, for example, with a piece of silicone elastomer similar to the cured shell. In some embodiments, the transponder is introduced into the breast implant during the shell patching (through the opening in the shell before the shell is patched). The patch is preferably secured by high pressure and heat. Alternatively, an adhesive or other method may be used to secure the patch. The patched silicone elastomer shell may be dried and cured, and is then filled (e.g., by a syringe) through a hole in the patch system (including the area where the patch joins with the shell) to a predetermined weight with fluid or gel. In some embodiments, the transponder is added during the silicone gel filling, through the hole used for the silicone gel filling. As shown in FIG. 1, in some embodiments, a highly viscous and highly elastic silicone gel is mixed and used (uncured) for filling the breast implant. The silicone gel may include a platinum catalyst. The filled implant is then placed in a vacuum chamber, where it undergoes one or more cycles of vacuum. If there are any bubbles still visible, additional vacuum cycles may be added.

The hole through which the implant was filled is then sealed (e.g., with an RTV silicone adhesive), and the silicone gel is cured. Preferably, the gel curing comprises high temperature curing (e.g., about 160° C.). In some embodiments, the implant may be filled with liquid or alternate fillers, which do not need further curing or vacuum cycles. The breast implant may then be cooled down to room temperature and placed in primary packaging (e.g., a double pack comprising a pair of implants). Sterilization may then be performed. Sterilization is preferably performed using dry heat (e.g., about 120 to 130° C. for about 24 to 48 hours). Alternatively, the implant may be sterilized using other sterilization methods, such as ethylene oxide.

Product labeling and secondary packaging processes are then performed before the final release of the product. In some embodiments, for example, product labeling assigns a serial number to the implant, and stores the serial number with information about the associated implant in a computer database (e.g., in an ERP system). Secondary packaging assigns the transponder identification code (e.g., 16 digit code) with the serial number of the implant. Product final release verifies that the transponder identification code matches the serial number of the implant. In other embodiments, different labeling/packaging processes may be used, as long as they match the transponder identification number to the serial number of each device.

Notably, Applicant has determined that the placement of the transponder within the breast implant is important for safe and effective function of the invention. For example, in some embodiments, the transponder may be affixed to the breast implant shell. However, the transponder is fragile and could break and/or could puncture the implant shell, thus it is preferred to place the transponder in a stronger part of the product. Accordingly, in other, more preferred embodiments, the transponder is suspended within the implant filling, close to the patch.

Figure 2:
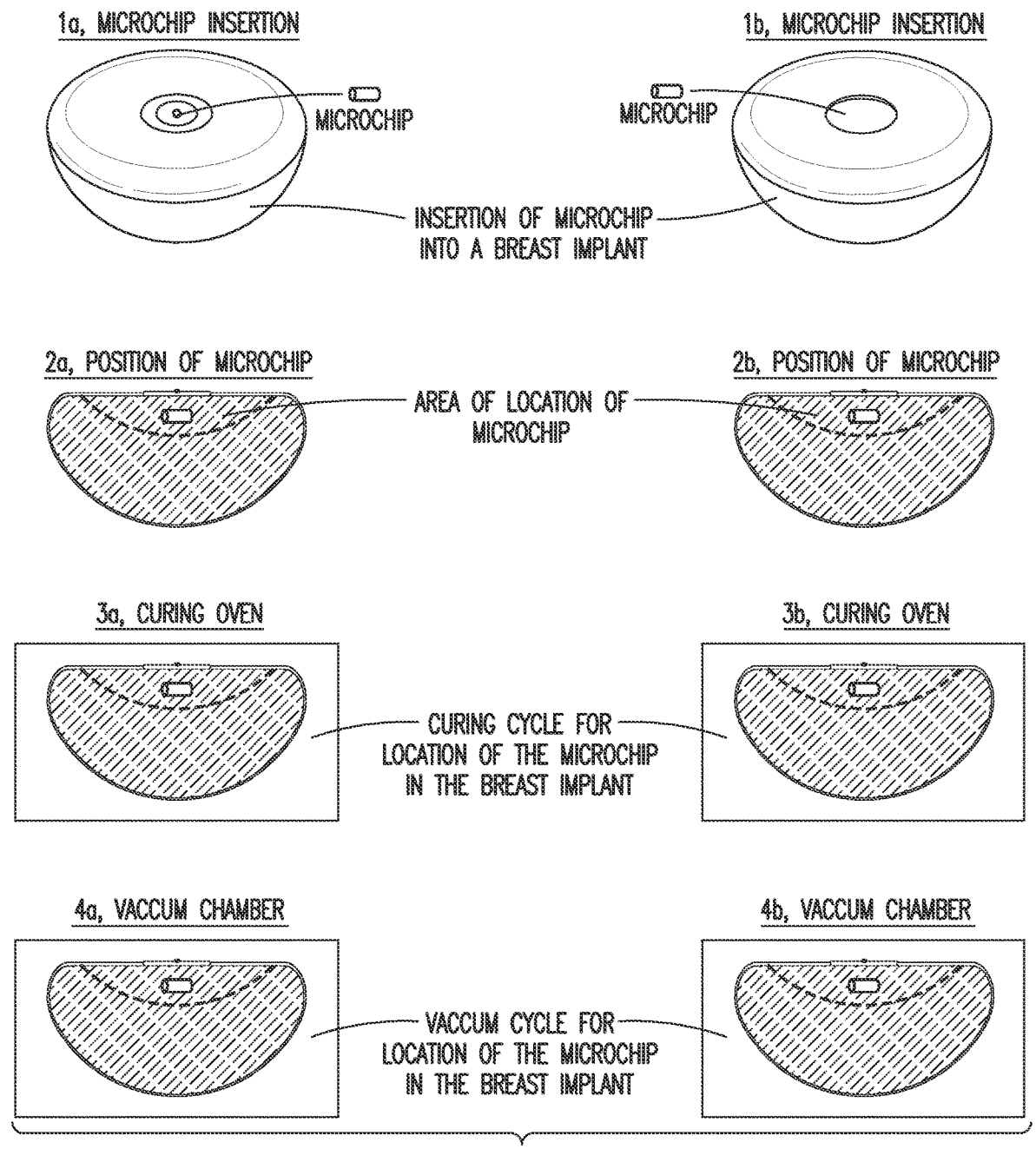
FIG. 2 shows a schematic diagram of breast implants of the present invention, according to some embodiments, illustrating exemplary placement of a microchip/transponder.

As indicated in FIG. 1, the transponder (microchip) can be added to the implant at different parts of the manufacturing process. For example, as shown in FIG. 2, the transponder can be incorporated during the Shell Patching (through the opening in the shell before patching; 1b). Alternatively, the transponder can be incorporated during the Silicone Gel Filling (through the hole in the patch system used for silicone gel filling; 1a).

In preferred embodiments, the transponder in the silicone gel is free floating, but in close proximity to the patch, which is at the back side of the implant (FIG. 2; 2a, 2b). Accordingly, once implanted, the transponder will be farthest from the exterior of the patient, which can protect the transponder and also ensure that it will not be felt (e.g., under the patient's skin when touched). The density of the silicone gel mixed for the implant filling is thus chosen so that the transponder will float in the silicone gel near the surface (the patch area). The transponder placement in the silicone filling gel at the back of the patch system is adjusted/fixed during the vacuum process (FIG. 2; 4a, 4b), and is verified when the filling hole is sealed.

Preferably, the transponder is added before the silicone gel is cured, so that is secured by the silicone. If the transponder is added after curing, it will break the gel when it is inserted and will not be well-integrated. The transponder placement in the silicone gel near the patch is further adjusted/fixed during the gel curing process (FIG. 2; 3a, 3b). Advantageously, when the gel is cured with the transponder embedded therein, the transponder is flexibly fixed in the gel, and like a rubber band will come back to the same location even when the implant is manipulated/deformed and the transponder is moved therein.

As described above and shown in FIG. 1, several breast implant manufacturing steps involve high temperatures, and high and low pressures. For example, gel curing may use a temperature up to about 200° C. (e.g., between 120° C. and 190° C.) for up to 8 hours. Sterilization may use a temperature up to about 150° C. (e.g., between 110° C. and 145° C.) for up to 48 hours. Transponders integrated within the implants as described herein, must be able to withstand such manufacturing conditions.

Advantageously, the present invention uses a high temperature-stable glass encapsulated transponder, which can withstand temperatures up to 210° C. (t 20° C.) and can be integrated into the body of the breast implant during the manufacture of the implant without loss of function thereafter. Such transponders are described in co-pending U.S. application Ser. No. 14/027,896, entitled "High Temperature Transponders," which is incorporated herein by reference in its entirety. In addition to their resistance to heat changes, these transponders provide good shock resistance, long term reliability, long range sensitivity, and small size, among other advantages.

While there have been shown and described fundamental novel features of the invention as applied to the preferred and exemplary embodiments thereof, it will be understood that omissions and substitutions and changes in the form and details of the disclosed invention may be made by those skilled in the art without departing from the spirit of the invention. Moreover, as is readily apparent, numerous modifications and changes may readily occur to those skilled in the art. Hence, it is not desired to limit the invention to the exact construction and operation shown and described and, accordingly, all suitable modification equivalents may be resorted to falling within the scope of the invention as claimed. It is the intention, therefore, to be limited only as indicated by the scope of the claims appended hereto.

The invention claimed is:

1. A method of identifying an implant, the method comprising:
    locating an external reader near the implant, the implant including:
        a shell having one or more layers surrounding a cavity;
        a filler disposed within the cavity;
        an opening extending through the shell and into the cavity;
        a patch disposed on an outermost surface of the shell, the patch configured to cover the opening; and
        a transponder unconnected to the shell, disposed within the cavity and flexibly fixed within the filler, the transponder spaced from the patch and proximate to the patch;

establishing wireless communication between the external reader and the transponder; and
identifying the implant using information obtained during the wireless communication.

2. The method of identifying the implant of claim 1, comprising:
accessing one or more databases containing identification information.

3. The method of identifying the implant of claim 1, wherein establishing the wireless communication between the external reader and the transponder includes communicating a unique identification code from the transponder to an external reader;
wherein the transponder is disposed within a gel in the implant.

4. The method of identifying the implant of claim 3, wherein the filler includes a silicone gel.

5. The method of identifying the implant of claim 1, wherein establishing the wireless communication includes establishing communication between the external reader and the transponder, the transponder positioned closer to a posterior side of the implant than an anterior side of the implant.

6. The method of identifying the implant of claim 1, wherein the transponder is sized to fit through the opening extending through the shell.

7. The method of identifying the implant of claim 1, wherein the patch is on a posterior side of the implant.

8. A method of identifying an implant located in a body, the method comprising:
locating the implant with an external reader, the implant including:
a multilayered shell surrounding a cavity;
a transponder positioned in the cavity of the implant;
a filler disposed within the cavity;
wherein the transponder is unconnected to the multilayered shell, suspended and secured within the filler; and
a patch disposed on the shell;
wherein the transponder is spaced from the patch;
wherein the transponder is proximate to the patch;
establishing communication between an external reader and the transponder; and
identifying the implant using information communicated to the external reader.

9. The method of identifying the implant of claim 8, further comprising:
accessing one or more databases containing identification information to identify the implant.

10. The method of identifying the implant of claim 8, wherein the transponder is configured to be implanted in the cavity concurrently with filling the cavity.

11. The method of identifying the implant of claim 8, wherein the filler includes a silicone gel.

12. The method of identifying the implant of claim 8, wherein the transponder is an RFID transponder.

13. The method of identifying the implant of claim 8, wherein the patch is located on a posterior side of the implant.

14. The method of identifying the implant of claim 13, wherein the transponder is located closer to the posterior side of the implant than an anterior side of the implant.

15. The method of identifying the implant of claim 8, wherein the implant is a breast implant.

16. The method of identifying the implant of claim 8, wherein the external reader includes a handheld scanner.

17. The method of identifying the implant of claim 8, wherein the filler is configured to be cured.

18. A system for identifying an implant, the system comprising:
an external reader configured to locate the implant, the implant including:
a multilayered shell forming a cavity;
a filler disposed within the cavity;
an aperture formed in back side of the multilayered shell;
a patch positioned over the aperture; and
a transponder unconnected to the multilayered shell, and suspended and flexibly fixed in the filler;
wherein the transponder is flexibly fixed within the filler proximate to the patch;
the external reader configured to read information contained on the transponder; and
a computer configured to receive communication from the external reader, the computer including:
a processor; and
a database containing information about the implant.

19. The system for identifying the implant of claim 18, wherein the transponder is located closer to a posterior side of the implant than an anterior side.

20. The system for identifying the implant of claim 18, wherein the implant is a breast implant.

* * * * *